Figure 1:
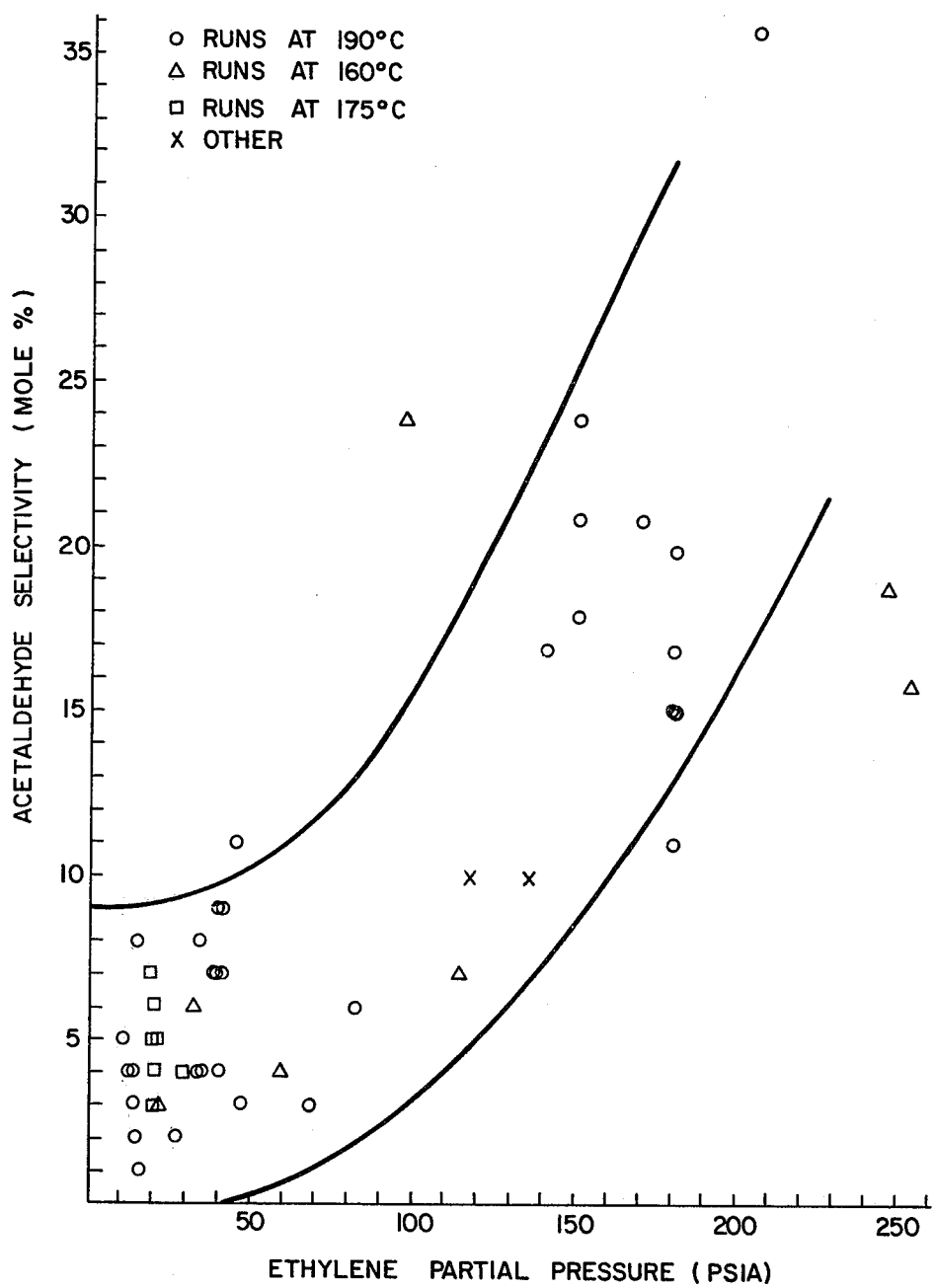

United States Patent [19]

Wood

[11] 4,387,255
[45] Jun. 7, 1983

[54] PROCESS FOR PRODUCTION OF ETHYLENE GLYCOL

[75] Inventor: George R. Wood, Wheaton, Ill.

[73] Assignee: Standard Oil Company (Indiana), Chicago, Ill.

[21] Appl. No.: 305,548

[22] Filed: Sep. 25, 1981

[51] Int. Cl.³ .................... C07C 29/50; C07C 31/20
[52] U.S. Cl. .................................................. 568/860
[58] Field of Search ........................................ 568/860

[56] References Cited

U.S. PATENT DOCUMENTS

| | | | |
|---|---|---|---|
| 1,982,545 | 11/1934 | Skarblom | 568/860 |
| 3,928,474 | 12/1975 | Witheford | 568/860 |
| 4,045,500 | 8/1977 | Onsayer et al. | 568/860 |
| 4,061,868 | 12/1977 | Fumagalli et al. | 568/860 |
| 4,195,190 | 3/1980 | Bierschenk et al. | 568/860 |
| 4,202,995 | 5/1980 | Mee | 568/860 |
| 4,209,650 | 6/1980 | Onsager et al. | 568/860 |

FOREIGN PATENT DOCUMENTS 2050376  1/1981  United Kingdom ................ 568/860

*Primary Examiner*—Joseph E. Evans
*Attorney, Agent, or Firm*—Stephen L. Hensley; William H. Magidson; William T. McClain

[57] ABSTRACT

Process for production of ethylene glycol comprising contacting a nonflammable feed comprising ethylene, molecular oxygen and water with a catalyst comprising iodine under reaction conditions in a reaction zone in which there is maintained a partial pressure of ethylene that is effective to yield ethylene glycol without substantial acetaldehyde generation. In a preferred embodiment, ethylene glycol is removed from the reaction zone at a rate effective to minimize formation of condensed glycol by-products.

5 Claims, 2 Drawing Figures

PROCESS FOR PRODUCTION OF ETHYLENE GLYCOL

BACKGROUND OF THE INVENTION

This invention relates to the production of ethylene glycol, and more particularly, to a process for production of ethylene glycol wherein levels of by-products are reduced.

Ethylene glycol is a well-known chemical useful in a number of commercial applications such as preparation of antifreeze compositions and certain polyesters.

A variety of processes for production of ethylene glycol has been proposed. For example, U.S. Pat. No. 1,982,545 (Skarblom) discloses a process comprising contacting ethylene, oxygen and water in the presence of an iodine-containing catalyst such that the following reactions occur:

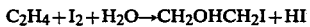

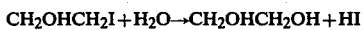

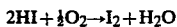

The net reaction is as follows:

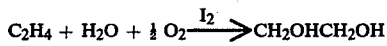

According to Skarblom, reaction conditions such as temperature, pressure and reactant concentrations and partial pressures are not critical except to the extent that they affect reaction rates.

Despite the apparent simplicity of the process according to Skarblom, the same is not entirely satisfactory, in part, because undesirably high levels of by-products typically are produced. Such by-products include acetaldehyde and condensed glycols such as diethylene glycol and p-dioxane. In a sense, formation of condensed glycols does not constitute a loss of reactants because these by-products equilibrate with the ethylene glycol. Acetaldehyde, on the other hand, does not undergo such equilibration, and accordingly, its production does result in a loss of reactants and decreased yield of the desired product.

Methods to reduce by-product formation in the Skarblom process have met with varying degrees of success. U.S. Pat. No. 3,928,474 (Witheford) discloses a process for production of ethylene glycol wherein the iodine-catalyzed reaction of ethylene, oxygen and water is conducted under superatmospheric pressure after which a distillation step is conducted at subatmospheric pressure. According to a further aspect of Witheford, the iodine-catalyzed reaction of ethylene, oxygen and water is conducted under superatmospheric pressure in two separate reaction zones, one containing an ethylene-rich feed and the other containing an oxygen-rich feed, followed by distillation under subatmospheric pressure such that condensed glycol formation is reduced and free iodine and organoiodine by-products are removed from the ethylene glycol in the distillation step. In Witheford's examples, preparation of ethylene glycol in 75% yield based upon consumed ethylene is illustrated. The yield of by-product condensed glycols was 8% (7% diethylene glycol and 1% triethylene glycol).

Although the process according to Witheford is reported to give reduced levels of condensed glycols as compared to the Skarblom process, the former is disadvantageous in that additional equipment is required. Further, Witheford does not provide for limiting formation of acetaldehyde or removal thereof. This deficiency is discussed in greater detail in U.S. Pat. No. 4,045,500 (Onsager et al.) which teaches that by-product acetaldehyde from the Skarblom or Witheford processes is inherently recycled to the reaction zone and converted to acetic acid which reacts with ethylene glycol and higher glycols to form acetates which are difficult to remove from the desired product. According to Onsager et al., this difficulty is remedied by separating the product obtained by the iodine-catalyzed reaction of ethylene, oxygen and water into a low-boiling fraction containing acetaldehyde, an ethylene glycol fraction and a high-boiling fraction containing higher glycols. The ethylene glycol fraction is removed for purification and acetaldehyde is separated from the low-boiling fraction. The low-boiling fraction remaining after separation as well as the higher-boiling fraction are recycled to the reaction zone. Ethylene glycol and higher glycols equilibrate in the reaction zone with the result that after a certain level of higher glycols has built up, further generation of such materials is suppressed.

While Onsager et al. does provide for removal of by-product acetaldehyde from ethylene glycol, there is no attempt to limit production of the by-product. Thus, raw materials otherwise convertible to the desired product are lost. Further, Onsager et al. requires handling of large amounts of higher glycols which can be disadvantageous from the standpoint of process efficiency.

From the foregoing it can be appreciated that it would be desirable to provide an improved process for production of ethylene glycol wherein the abovedescribed problems are reduced or eliminated. It is an object of this invention to provide an improved, iodine-catalyzed process for production of ethylene glycol. A further object is to provide a process wherein generation of by-product acetaldehyde is retarded. A further object is to provide a process in which generation of both acetaldehyde and condensed glycols is retarded. A still further object of the invention is to provide a process in which high selectivity to ethylene glycol is attained with reduced loss of raw materials through by-product formation. Other objects of the invention will be apparent to persons skilled in the art from the following description and the appended claims.

I have now found that the objects of this invention can be attained by contacting a nonflammable feed comprising ethylene, oxygen and water with a catalyst comprising iodine under reaction conditions in a reaction zone in which there is maintained a relatively low partial pressure of ethylene. Surprisingly, maintenance of low ethylene partial pressures in the reaction zone results in decreased formation of acetaldehyde, and accordingly, reduced loss of raw materials through by-product formation. As a result, selectivity to ethylene glycol is increased. This is in contrast to the aforesaid patents which suggest that ethylene partial pressure is important only from the standpoint of reaction rate. While ethylene partial pressure does influence reaction rate, the large values proposed and preferred by the prior art are, in fact, detrimental to the attainment of maximum selectivity to ethylene glycol.

According to a further aspect of this invention, formation of condensed glycol by-products is retarded by maintaining a relatively low level of ethylene glycol in the reaction zone. The relationship between ethylene glycol levels and condensed glycol formation, while not a directly proportional one, is such that prompt removal of ethylene glycol can result in substantial reductions in formation of condensation products thereof. This, of course, leads to greater selectivity to ethylene glycol and there is reduced need for costly by-product removal operations.

DESCRIPTION OF THE INVENTION

Briefly, this invention provides an improved process for production of ethylene glycol comprising contacting a nonflammable feed comprising ethylene, oxygen and water with a catalyst comprising iodine under reaction conditions in a reaction zone in which there is maintained an ethylene partial pressure effective to yield ethylene glycol without substantial formation of acetaldehyde. According to a further aspect of the invention, the concentration of ethylene glycol in the reaction zone is maintained at a level that is sufficiently low to avoid substantial formation of condensed glycol by-products.

In greater detail, ethylene partial pressures employed according to this invention preferably are high enough to yield a product comprising ethylene glycol and less than about 10 mole % acetaldehyde based upon total reaction products. More preferably, ethylene partial pressure ranges from about 5 to about 100 psia (about 0.4 to about 7 kg/cm$^2$ absolute) in order to attain desirable reaction rates while limiting acetaldehyde formation. Most preferably, ethylene partial pressure ranges from about 20 to about 80 psia (about 1.4 to about 5.6 kg/cm$^2$ absolute), best results being attained at about 30 to about 40 psia (about 2.1 to about 2.8 kg/cm$^2$ absolute).

Oxygen partial pressure is not critical, though at low partial pressures, reaction rates may be lower than desired. Oxygen partial pressures that are preferred from the standpoint of attaining desirable reaction rates range from about 5 to about 50 psia (about 0.35 to about 3.5 kg/cm$^2$), best results being attained at about 20 to about 35 psia (about 1.4 to about 21.4 kg/cm$^2$).

The concentrations of ethylene and oxygen in the reaction zone are such that a nonflammable feed is formed. Specific concentrations outside the flammable range can be determined by persons skilled in the art by reference to standard flammability diagrams such as that appearing in U.S. Bureau of Mines Bulletin 503. For a given ethylene concentration, preferred oxygen concentration is just below the flammable limit.

For given ethylene and oxygen partial pressures, concentrations can be adjusted to insure operation outside the flammable region through the use of diluent gas. In fact, it is preferred to employ diluent gas because use of the same can result in sufficient dilution of oxygen concentration to permit operation at partial pressures that would otherwise yield flammable mixtures of ethylene and oxygen. Suitable diluent gases are those that are substantially inert with respect to the reactants and remain in the gaseous state under reaction conditions. Specific examples include methane, ethane, propane, butane and other relatively low boiling, inert hydrocarbons. Mixtures of diluent gases also can be used. A preferred diluent gas is ethane due to its low cost and inertness. Preferred diluent gas partial pressures range from about 15 to about 700 psia (about 1 to about 49 kg/cm$^2$) in order to provide suitable dilution while avoiding operation at excessively high overall pressures.

Overall reaction zone pressure varies depending on ethylene and oxygen partial pressures, solvent vapor pressure at the temperature of operation and diluent partial pressure, if any. At its lower level, overall pressure is at least sufficient to maintain a liquid phase in the reaction zone. Preferably, overall pressure is at least about 50 psia (about 3.5 kg/cm$^2$) in order to insure maintenance of a liquid phase. More preferably, overall pressure ranges from about 50 to about 800 psia (about 3.5 to about 56 kg/cm$^2$) in order to insure the presence of a liquid phase while avoiding excessive need for costly high pressure equipment. Best results are attained at about 250 to about 500 psia (about 18 to about 35 kg/cm$^2$).

In other respects, the iodine-catalyzed reaction of ethylene, oxygen and water according to this invention is conducted under conditions substantially in accord with the aforesaid Skarblom, Witheford and Onsager et al. patents which are incorporated herein by reference.

Suitable catalysts include a variety of materials capable of liberating iodine under reaction conditions. Specific examples of such materials include iodine, hydrogen iodide, metal iodides such as ferrous iodide, cuprous iodide, zinc iodide, and organoiodine compounds such as 1,2-diiodoethane, and iodohydrin. Mixtures of iodine containing materials can be used if desired as can mixtures of iodine-containing materials with various additives such as elemental metals, e.g., copper; metal oxides, e.g., cuprous oxide, manganous oxide and ferrous oxide; active carbon; and metal nitrates, e.g., sodium nitrate.

The amount of catalyst employed according to the invention is a catalytically effective amount. This amount will vary depending upon such factors as choice of catalyst, reactor capacity, production rate, etc. Preferably, catalyst is employed in an amount effective to provide from about 0.1 to about 25 wt.% equivalents of atomic iodine based upon total liquid reaction mixture. More preferably, catalyst concentration ranges from about 5 to about 15 wt.% atomic iodine equivalents in order to attain a high production rate. The balance of the liquid reaction mixture comprises water at the start of the process or water and products during the course of the process. Water functions as both a reactant and solvent for the reaction. Of course, some of the water may be replaced by other suitable solvents. Preferably, at least about 50 wt.% of the liquid reaction mixture at any given time is water. More preferably, at least about 75 wt.% is water.

Reaction temperature is sufficiently high that the reaction proceeds at a reasonable rate and without substantial iodoethanol formation but not so high that substantial burning of ethylene to carbon oxides occurs. Preferred temperatures range from about 100° to about 250° C., best results being attained at about 125° to about 200° C.

The process can be operated on a continuous or batchwise basis, the former being preferred. In either case, makeup gases and water are added as needed to maintain appropriate concentrations in the reaction zone.

Reaction times vary depending on temperature, pressure, catalyst concentration, production rate, operational mode and other factors that can be determined by persons skilled in the art. In batch processes operated under the preferred conditions described hereinabove, typical reaction times range from about ¼ to about 2 hours. In continuous processes, reaction zone residence times can be regulated as desired.

The reaction zone employed according to this invention can be made up of a single reactor or a plurality of reactors operated in series. Due to the corrosivity of iodine, reactors should be constructed of a corrosion resistant material such as titanium or Hastalloy.

During or on termination of reaction in batch processes, or during the course of a continuous process, gaseous and liquid effluent is removed from the reaction zone. Gaseous effluent typically comprises carbon oxides, diluent gas, if used, and unreacted ethylene and oxygen as well as by-product acetaldehyde. In continuous processes, unreacted ethylene and oxygen and diluent gas, if used, can be recycled to the reaction zone after separation of acetaldehyde and carbon oxides therefrom. Liquid effluent typically comprises ethylene glycol, higher-boiling condensed glycol by-products such as diethylene glycol and p-dioxane, organic iodine compounds such as iodohydrin and iodotriethylene glycol, and minor amounts of by-product acetaldehyde. Ethylene glycol is separated from the liquid effluent by conventional separation techniques such as fractional distillation, absorption or extraction. High-boiling condensed glycol by-products can be separated from the effluent by similar techniques after which the remaining liquid effluent can be recycled to the reaction zone. In the alternative, condensed glycols can be returned to the reaction zone to equilibrate with ethylene glycol in accordance with the aforesaid Onsager et al. patent in order to limit condensed glycol generation. Total acetaldehyde in the gaseous and liquid effluents typically ranges up to about 10 mole % based on total reaction products. Preferably, total acetaldehyde is less than about 8 mole %.

According to a preferred embodiment of this invention, liquid effluent is removed from the reaction zone at a rate sufficient to maintain a low level of ethylene glycol in the reaction zone and thereby minimize formation of condensed glycol by-products. Preferably, the rate of removal of liquid effluent is such that the concentration of ethylene glycol in the reaction zone is negligible, although this requires handling of substantial amounts of water in view of its lower boiling point than that of ethylene glycol. In view of these considerations, it is more preferred to remove liquid effluent at a rate such that separation costs are balanced against losses in yield due to formation of condensed glycols. The amount of ethylene glycol to be retained in the reaction zone will vary depending on choice of separation technique and other operating factors and can be determined by persons skilled in the art by routine experimentation. Preferably, removal is at a rate sufficient to maintain an ethylene glycol concentration of about 2 to about 4 wt.%, based on total reactor effluent.

According to this embodiment of the invention, when liquid effluent is promptly removed from the reaction zone to maintain low levels of ethylene glycol therein and thereby reduce formation of condensed glycol by-products, ethylene glycol is separated from the liquid effluent by fractional distillation, absorption, extraction or other suitable techniques. Higher boiling materials such as condensed glycols then are removed from the remaining effluent and the remainder can be recycled to the reaction zone.

The following examples illustrate the present invention and are not to be construed as limiting the scope thereof.

EXAMPLE I

A series of runs was conducted in a stirred, one liter titanium autoclave equipped with a liquid sampling valve, heating mantle, cooling coils and condenser according to the following general procedure. 300 g aqueous iodine solution prepared by dissolving, in water, weighed amounts of iodine and/or hydrogen iodide corresponding to the levels specified in Table I were added to the reactor and stirred at 1500 rpm. Heating of the reactor to reaction temperature was begun and ethylene, oxygen and ethane were continuously charged at a rate sufficient to maintain a total flow rate of 130 STP l/hr and under pressures such that overall reactor pressure was maintained at 400 psig. Ethylene and oxygen partial pressures were varied as shown in Table I.

Reaction was allowed to continue for varying lengths of time, as specified in Table I (reaction time does not include time required for heating of the reactor), after which the flow of ethylene and oxygen was discontinued and the reactor was cooled to terminate the reaction. The reaction product then was sampled and ethylene glycol concentration was determined by periodate oxidation. Distribution of ethylene moieties in the liquid and gaseous products was determined by gas chromatography.

Reaction conditions are reported in Table I and results in Table II. As used in Table II and subsequent tables, EGC represents ethylene glycol concentration in wt %, RR represents ethylene glycol reaction rate in g-moles EG/kg-hr, EG represents ethylene glycol, AA represents acetaldehyde, DI represents dioxane, DE represents diethylene glycol, E represents ethanol and $CO_x$ represents the sum of CO and $CO_2$ in mole % based on total product.

TABLE I

| | | (Reaction Conditions) | | | | |
|---|---|---|---|---|---|---|
| RUN NO. | TEMPERATURE (°C.) | PARTIAL PRESSURES (psia) | | CATALYST (mmole/ 100 g) | | TIME (min.) |
| | | $C_2H_4$ | $O_2$ | $I_2$ | HI | |
| 1* | 190 | 180 | 11 | 4.0 | 10.1 | 32 |
| 2 | 190 | 170 | 8 | 4.0 | 10.0 | 121 |
| 3 | 190 | 150 | 9 | 4.0 | 10.0 | 120 |
| 4 | 190 | 140 | 16 | 4.0 | 10.0 | 120 |
| 5 | 190 | 40 | 13 | 5.1 | 10.0 | 52 |
| 6 | 190 | 39 | 14 | 5.0 | 10.0 | 90 |
| 7 | 190 | 34 | 20 | 5.0 | 10.0 | 120 |
| 8 | 127 | 135 | 27 | 25.0 | 50.0 | 90 |
| 9 | 148 | 117 | 16 | 25.0 | 50.0 | 90 |
| 10 | 160 | 32 | 20 | 25.0 | 50.0 | 60 |

*Gas flow rate was 260 STP l/hr in this run.

TABLE II

| | | | (Results) | | | | | |
|---|---|---|---|---|---|---|---|---|
| RUN NO. | EGC | RR | PRODUCT DISTRIBUTION (mole % $C_2H_4$ moieties) | | | | | |
| | | | EG | AA | DI | DE | E | $CO_x$ |
| 1 | 2.4 | 0.54 | 77 | 20 | 1 | 3 | 0 | 0 |
| 2 | 3.9 | 0.31 | 71 | 21 | 3 | 5 | 0.6 | 0 |
| 3 | 5.6 | 0.40 | 72 | 21 | 3 | 5 | 0.3 | T* |
| 4 | 9.4 | 0.69 | 70 | 17 | 5 | 9 | 0.2 | 0.6 |
| 5 | 5.2 | 0.82 | 83 | 9 | 3 | 5 | 0.1 | 0.7 |
| 6 | 7.3 | 0.58 | 77 | 7 | 5 | 12 | 0.1 | 2.0 |
| 7 | 11.2 | 0.58 | 77 | 8 | 6 | 9 | 0.2 | 3.7 |
| 8 | 4.8 | 0.51 | 79 | 10 | 5 | 6 | 0 | 0.2 |
| 9 | 10.9 | 1.09 | 68 | 10 | 9 | 13 | 0 | 0.5 |

TABLE II-continued

| RUN NO. | (Results) PRODUCT DISTRIBUTION (mole % $C_2H_4$ moieties) | | | | | | | |
|---|---|---|---|---|---|---|---|---|
| | EGC | RR | EG | AA | DI | DE | E | $CO_x$ |
| 10 | 9.1 | 1.53 | 68 | 6 | 12 | 13 | 0.1 | 1.3 |

*In this and all subsequent tables, T stands for trace.

From Example I and Tables I and II it can be seen that operation at relatively low ethylene partial pressures in accordance with the invention (runs 5–7 and 10) resulted in comparable or better selectivity to ethylene glycol and substantially reduced acetaldehyde levels as compared to the comparative runs (1–4 and 8–9) operated at high ethylene partial pressures. It also is to be noted that the quotient of EGC and TIME, expressed as wt.% EG/hr, ranged from 4.9–6.0 for the 190° C. runs at low ethylene partial pressure as opposed to 1.9–4.7 for the 190° C. runs at higher ethylene partial pressure. Comparison of wt.% EG/hr for runs 8–10 reveals a similar result through the comparison is less direct due to differences in reaction temperature.

EXAMPLE II

Another series of runs was conducted according to the procedure of Example I except as indicated. Temperature in all runs was 160° C. Reaction conditions are reported in Table III and results in Table IV.

TABLE III

| RUN NO. | (Reaction Conditions) | | | | |
|---|---|---|---|---|---|
| | PARTIAL PRESSURES (psia) | | CATALYST (mmole/ 100 g) | | TIME (min) |
| | $C_2H_4$ | $O_2$ | $I_2$ | HI | |
| 11(1) | 254 | 12 | 19.9 | 10.0 | 90 |
| 12(1) | 247 | 13 | 20.0 | 10.1 | 37 |
| 13(2) | 114 | 20 | 10.0 | 0 | 90 |
| 14(3) | 96 | 12 | 0 | 217.0 | 90 |
| 15(4) | 59 | 27 | 0 | 0 | 120 |
| 16(2) | 21 | 30 | 10.0 | 0 | 120 |

(1)In these runs the reaction mixture included 10 wt. % Amoco active carbon (grade PX-21).
(2)In these runs the reaction mixture included 2.3 wt. % Amoco active carbon (grade PX-21).
(3)In this run the reaction mixture included 100 mmole/100 g of CuO and 18 mmole/100 g of $Cu_2O$.
(4)In this run the reaction mixture contained 20 mmole/100 g $FeI_2$.

TABLE IV

| RUN NO. | (Results) PRODUCT DISTRIBUTION (mole % $C_2H_4$ moieties) | | | | | | | |
|---|---|---|---|---|---|---|---|---|
| | EGC | RR | EG | AA | DI | DE | E | $CO_x$ |
| 11 | 2.1 | 0.55 | 74 | 16 | 8 | 1 | 1 | 6.7 |
| 12 | 1.5 | 0.55 | 76 | 19 | 4 | 0.4 | 1 | 3.8 |
| 13 | 4.3 | 0.44 | 83 | 7 | 6 | 4 | 0 | 2.4 |
| 14 | 8.0 | 2.05 | 51 | 24 | 15 | 10 | 0.3 | 1.9 |
| 15 | 4.8 | 0.36 | 81 | 4 | 4 | 6 | 6.0 | 2.5 |
| 16 | 3.7 | 0.34 | 88 | 3 | 6 | 3 | 0 | 11.0 |

From this example and the tables, it can be seen that operation at low ethylene partial pressure in runs 15 and 16 resulted in high selectivity to ethylene glycol with minimal acetaldehyde generation. The level of acetaldehyde in run 14 is higher than would have been expected on the basis of runs 11–13, 15 and 16, possibly due to the presence of the copper oxides or high iodine concentration in the reaction mixture. With the exception of run 14, wt.% EG/hr was generally comparable for the lower and higher ethylene partial pressure runs.

EXAMPLE III

Another series of runs was conducted according to the procedure of Example I except as indicated. Temperature in all runs was 175° C. Reaction conditions and results are reported in Tables V and VI respectively.

TABLE V

| RUN NO. | (Reaction Conditions) | | | | |
|---|---|---|---|---|---|
| | PARTIAL PRESSURES (psia) | | CATALYST (mmole/ 100 g) | | TIME (min.) |
| | $C_2H_4$ | $O_2$ | $I_2$ | HI | |
| 17(1) | 20 | 10 | 0.8 | 0 | 87 |
| 18(2) | 20 | 10 | 10.0 | 0 | 109 |
| 19(3) | 20 | 10 | 7.4 | 0 | 120 |
| 20 | 19 | 9 | 9.9 | 0 | 87 |
| 21(4) | 20 | 10 | 0 | 10.0 | 89 |
| 22(5) | 20 | 10 | 0.8 | 0 | 91 |
| 23(6) | 18 | 9 | 0.8 | 0 | 34 |

(1)Reaction mixture included 36.9 mmole/100 g 2-iodoethanol and 1.8 mmole/100 g 1,2-diiodoethane.
(2)Reaction mixture included 1.0 mmole/100 g Cu°.
(3)Reaction mixture included 15.1 mmole/100 g KI.
(4)Reaction mixture included 10.0 mmole/100 g NaI.
(5)Reaction mixture included 31.5 mmole/100 g 2-iodoethanol and 1.8 mmole/100 g 1,2-diiodoethane.
(6)In this run the solvent was a mixture of 50 wt. % dioxane and 50 wt. % water and the reaction mixture included 36.9 mmole/100 g 2-iodoethanol and 1.8 mmole/100 1,2-diiodoethane.

TABLE VI

| RUN NO. | (Results) PRODUCT DISTRIBUTION (mole % $C_2H_4$ moieties) | | | | | | | |
|---|---|---|---|---|---|---|---|---|
| | EGC | RR | EG | AA | DI | DE | E | $CO_x$ |
| 17 | 6.6 | 0.41 | 83 | 5 | 6 | 7 | 0 | ND* |
| 18 | 2.0 | 0.14 | 95 | 3 | 0 | 2 | 0 | 2.5 |
| 19 | 3.1 | 0.20 | 89 | 6 | 1 | 3 | 0 | ND |
| 20 | 1.3 | 0.10 | 88 | 7 | 2 | 4 | 0 | ND |
| 21 | 1.1 | 0.12 | 96 | 4 | 0 | 0 | 0 | ND |
| 22 | 6.1 | 0.29 | 86 | 4 | 4 | 6 | 0 | ND |
| 23 | 4.7 | 0.26 | 85 | 5 | (1) | 10 | 6 | ND |

*In this and all subsequent tables, ND stands for not determined.
(1) Not determined as solvent for the run included dioxane.

As can be seen from the above tables, operation at low ethylene partial pressures in runs 17–23 gave similar results at 175° C. and with variations in catalyst as the low ethylene partial pressure runs reported in Examples I and II and Tables I–IV.

EXAMPLE IV

A series of runs was conducted according to the procedure of Example I and at 190° C. except as otherwise noted. Conditions and results are reported in Tables VII and VIII respectively.

TABLE VII

| RUN NO. | (Reaction Conditions) | | | | |
|---|---|---|---|---|---|
| | PARTIAL PRESSURES (psia) | | CATALYST (mmole/ 100 g) | | TIME (min.) |
| | $C_2H_4$ | $O_2$ | $I_2$ | HI | |
| 24(1) | 16 | 8 | 9.4 | 0 | 88 |
| 25(2) | 40 | 14 | 10.2 | 0 | 95 |
| 26(3) | 40 | 14 | 0 | 20.0 | 59 |
| 27(4) | 205 | 3 | 0 | 20.0 | 114 |
| 28 | 180 | 5 | 10.0 | 0 | 125 |
| 29(5) | 180 | 8 | 4.9 | 9.9 | 153 |
| 30(5) | 180 | 8 | 4.7 | 9.4 | 180 |

TABLE VII-continued

| RUN NO. | PARTIAL PRESSURES (psia) | | | | CATALYST (mmole/100 g) | TIME (min.) |
|---|---|---|---|---|---|---|
| | $C_2H_4$ | $O_2$ | $I_2$ | HI | | |
| 31[5] | 180 | 8 | 4.8 | 9.6 | | 100 |

[1] Reaction mixture included 9.6 wt. % Amoco active carbon (grade PX-21).
[2] Reaction mixture included 2.3 wt. % Amoco active carbon (grade PX-21).
[3] Reaction mixture included 99.9 mmole/100 g KI.
[4] Reaction mixture included 99.8 mmole/100 g KI.
[5] Reaction mixture included 2.5 wt. % Amoco active carbon (grade PX-21).

TABLE VIII (Results)
PRODUCT DISTRIBUTION (mole % $C_2H_4$ moieties)

| RUN NO. | EGC | RR | EG | AA | DI | DE | E | $CO_x$ |
|---|---|---|---|---|---|---|---|---|
| 24 | 3.0 | 0.24 | 95 | 1 | 5 | 0 | 0 | 30.0 |
| 25 | 2.4 | 0.26 | 83 | 7 | 5 | 5 | 0 | 3.5 |
| 26 | 3.2 | 0.46 | 85 | 9 | 3 | 3 | 0 | 1.3 |
| 27 | 4.5 | 0.40 | 55 | 36 | 5 | 5 | 0 | 0.4 |
| 28 | 5.1 | 0.42 | 74 | 15 | 5 | 6 | 0 | 1.6 |
| 29 | 5.3 | 0.34 | 73 | 15 | 7 | 5 | 0.5 | ND |
| 30 | 10.7 | 0.34 | 64 | 11 | 9 | 16 | 0.2 | 1.6 |
| 31 | 7.7 | 0.51 | 64 | 17 | 11 | 8 | 0 | 1.1 |

Again, it can be seen that those runs carried out according to the present invention (runs 24–26) at relatively low ethylene partial pressures yielded less acetaldehyde than the comparative runs at higher ethylene partial pressures.

EXAMPLE V

Another series of runs was conducted at 190° C. according to Example I except as noted. Conditions and results are reported in Tables IX and X respectively.

TABLE IX

| RUN NO. | PARTIAL PRESSURES (psia) | | | | CATALYST (mmole/100 g) | TIME (min.) |
|---|---|---|---|---|---|---|
| | $C_2H_4$ | $O_2$ | $I_2$ | HI | | |
| 32[1] | 82 | 14 | 10.0 | 0 | | 120 |
| 33[1] | 45 | 12 | 10.0 | 0 | | 45 |
| 34[1] | 12 | 19 | 10.0 | 0 | | 20 |
| 35[2] | 15 | 21 | 5.0 | 0 | | 120 |
| 36 | 15 | 24 | 0 | 10.0 | | 33 |
| 37[3] | 14 | 23 | 10.0 | 0 | | 30 |
| 38[4] | 14 | 19 | 10.0 | 0 | | 120 |
| 39[5] | 11 | 15 | 20.0 | 0 | | 30 |
| 40[6] | 47 | 15 | 9.3 | 0 | | 121 |
| 41[6] | 68 | 14 | 9.3 | 0 | | 121 |
| 42[7] | 150 | 8 | 4.0 | 10.0 | | 121 |
| 43[8] | 150 | 8 | 4.0 | 4.8 | | 120 |
| 44[9] | 40 | 13 | 0 | 0 | | 77 |
| 45[10] | 41 | 18 | 0 | 10.0 | | 58 |
| 46[1] | 34 | 9 | 5.0 | 10.0 | | 90 |
| 47[1] | 35 | 11 | 5.0 | 10.0 | | 90 |
| 48[11] | 27 | 11 | 0 | 0 | | 90 |

[1] Reaction mixture included 2.3 wt. % Amoco active carbon (grade PX-21).
[2] Reaction mixture included 2.4 wt. % Amoco active carbon (grade PX-21). Oxygen cylinder was changed 51 minutes into the run.
[3] Reaction mixture included 2.3 wt. % MCB activated charcoal powder (Norit A).
[4] Reaction mixture included 4.6 wt. % MCB activated charcoal powder (Norit A).
[5] Reaction mixture included 10.0 wt. % MCB activated charcoal powder (Norit A).
[6] Reaction mixture included 4.3 wt. % MCB activated charcoal powder (Norit A).
[7] Reaction mixture included 10.0 mmole/100 g CuI.
[8] Reaction mixture included 10.0 mmole/100 g $FeI_2$.
[9] Reaction mixture included 20.0 mmole/100 g $FeI_2$.
[10] Reaction mixture included 100.0 mmole/100 g $FeI_2$.
[11] Reaction mixture included 2.3 wt. % Amoco active carbon (grade PX-21) and 10.0 mmole/100 g $FeI_2$.

TABLE X (Results)
PRODUCT DISTRIBUTION (mole % $C_2H_4$ moieties)

| RUN NO. | EGC | RR | EG | AA | DI | DE | E | $CO_x$ |
|---|---|---|---|---|---|---|---|---|
| 32 | 7.3 | 0.46 | 80 | 6 | 6 | 8 | 0 | 5.0 |
| 33 | 6.7 | 0.68 | 78 | 11 | 6 | 5 | 0 | 4.6 |
| 34 | 3.7 | 0.83 | 87 | 4 | 6 | 3 | 0 | 10.0 |
| 35 | 3.2 | 0.32 | 93 | 2 | 4 | 2 | 0 | 28.0 |
| 36 | 1.7 | 0.31 | 92 | 8 | T | 0.6 | 0 | 0.0 |
| 37 | 3.1 | 0.62 | 92 | 4 | 2 | 2 | 0 | 8.7 |
| 38 | 3.6 | 0.20 | 89 | 3 | 5 | 3 | 0.7 | 38.0 |
| 39 | 4.0 | 0 | 80 | 5 | 11 | 4 | 0.2 | 28 |
| 40 | 4.4 | 0.33 | 86 | 3 | 7 | 4 | 0 | 21 |
| 41 | 5.0 | 0.34 | 85 | 3 | 6 | 6 | 0 | 18 |
| 42 | 7.1 | 0.47 | 73 | 18 | 4 | 6 | 0.2 | 0.5 |
| 43 | 5.4 | 0.33 | 63 | 24 | 4 | 6 | 3.0 | 0.8 |
| 44 | 5.3 | 0.55 | 79 | 4 | 4 | 8 | 5.0 | 5.1 |
| 45 | 2.5 | 0.81 | 90 | 7 | 1 | 3 | 0.9 | 2.8 |
| 46 | 7.7 | 0.60 | 78 | 4 | 10 | 8 | 0.4 | 10.1 |
| 47 | 7.1 | 0.57 | 78 | 4 | 10 | 8 | T | 8.2 |
| 48 | 9.5 | 0.71 | 75 | 2 | 11 | 10 | 2.0 | 13.1 |

The relationship between acetaldehyde levels and ethylene partial pressures in Examples I–V, is shown graphically in FIG. 1. As can be seen, lower partial pressures led to reduced by-product formation.

Figure 2:
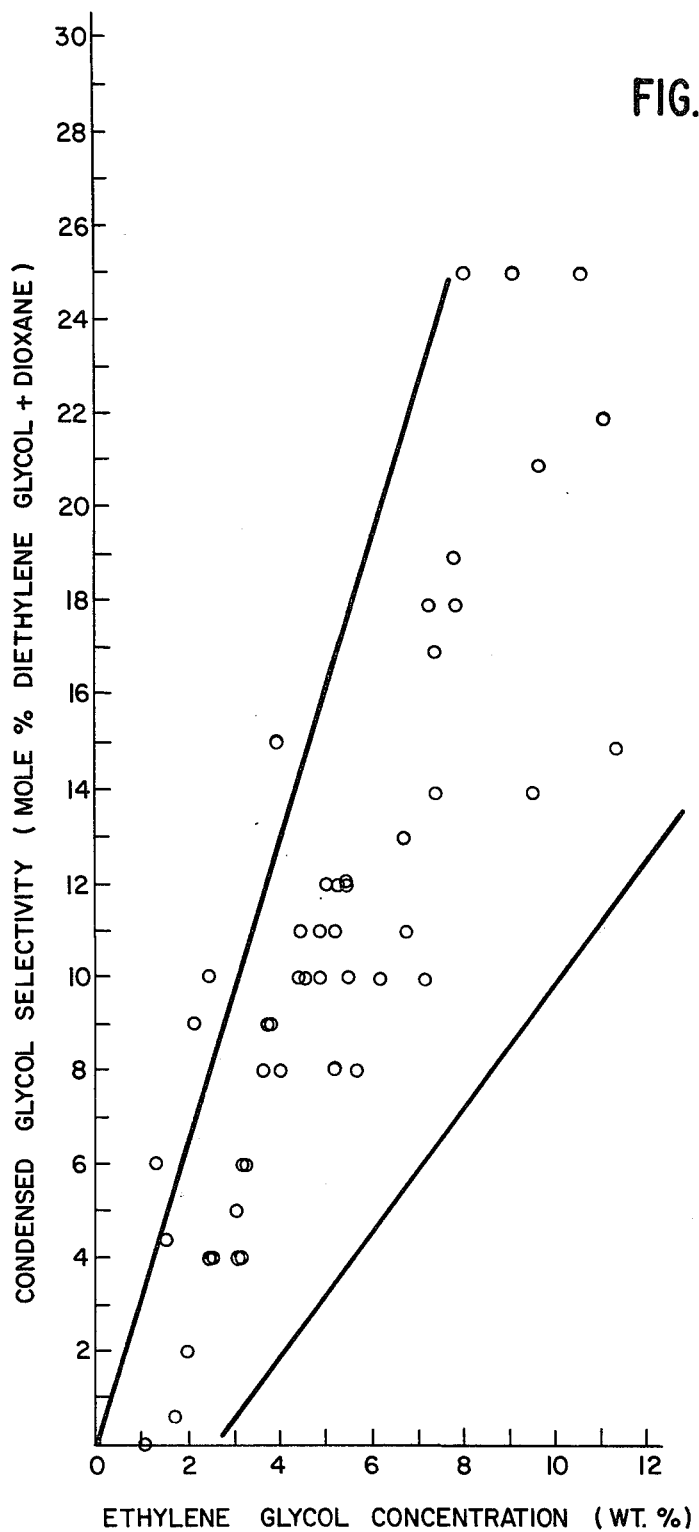

FIG. 2 presents a plot of condensed glycol selectivity (mole % DI plus DE) versus wt.% ethylene glycol in the final product for all runs except run 23 in which dioxane was not determined. It can be seen that condensed glycol formation was lower in runs in which ethylene glycol concentration was lower, and accordingly, that maintaining the level of ethylene glycol in the reaction zone at a low level can lead to reduced generation of condensed glycol by-products.

I claim:

1. A process for production of ethylene glycol comprising contacting a feed comprising reactants consisting essentially of ethylene, molecular oxygen and water with a catalyst comprising iodine at a temperature ranging from about 100° to about 250° C. and overall pressure of 50 to about 800 psia in a reaction zone in which the ethylene partial pressure ranges from about 30 to about 40 psia (about 2.1 to about 2.8 kg/cm²), oxygen partial pressure ranges from about 5 to about 50 psia (about 0.35 to about 3.5 kg/cm²) and ethane partial pressure ranges from about 15 to about 700 psia.

2. The process of claim 1 wherein the catalyst comprises iodine, hydrogen iodide, metal iodides, organic iodides or a mixture thereof.

3. The process of claim 2 wherein the catalyst concentration ranges from about 0.1 to about 25 wt.% of the total liquid reaction mixture expressed as equivalents of atomic iodine.

4. The process of claim 1 wherein the rate of removal of ethylene glycol from the reaction zone is such that ethylene glycol concentration ranges from about 2 to about 4 wt.%.

5. The process of claim 1 wherein the concentration of ethylene glycol in the reaction zone is maintained at a level effective to avoid substantial condensed glycol formation.

* * * * *